United States Patent [19]

Strandberg et al.

[11] Patent Number: 4,535,776

[45] Date of Patent: Aug. 20, 1985

[54] CARDIAC PACEMAKER WITH TWO UNIPOLAR ELECTRODES

[75] Inventors: Hans G. Strandberg, Sundbyberg; Hans Andersen, Vaellingby, both of Sweden

[73] Assignee: Siemens Aktiengesellschaft, Berlin and Munich, Fed. Rep. of Germany

[21] Appl. No.: 560,712

[22] Filed: Dec. 12, 1983

[30] Foreign Application Priority Data

Dec. 21, 1982 [DE] Fed. Rep. of Germany ....... 3247264

[51] Int. Cl.³ ............................................... A61N 1/36
[52] U.S. Cl. ............................................... 128/419 PG
[58] Field of Search ................................... 128/419 PG

[56] References Cited

U.S. PATENT DOCUMENTS 3,678,937 7/1972 Cole et al. .................... 128/419 PG
4,088,140 5/1978 Rockland et al. ............ 128/419 PG
4,312,355 1/1982 Funke .......................... 128/419 PG

OTHER PUBLICATIONS

Fischler et al, "IEEE Transactions on Biomedical Engineering," vol. 16, No. 1, Jan. 1969, pp. 64–68.

Primary Examiner—William E. Kamm
Attorney, Agent, or Firm—Karl F. Milde, Jr.

[57] ABSTRACT

To make it possible to suppress spurious signals of any type without having a negative effect on the stimulation or detection characteristics of a cardiac pacemaker, a signal processing unit is provided which prevents control signals from being applied to the device for controlling the heart stimulation pulses when signals from the two unipolar pacemaker electrodes are received at substantially the same time.

5 Claims, 5 Drawing Figures

CARDIAC PACEMAKER WITH TWO UNIPOLAR ELECTRODES

BACKGROUND OF THE INVENTION

The present invention relates to a cardiac pacemaker with two unipolar electrodes, at least one indifferent electrode arranged some distance away from these two unipolar electrodes, a series-connected amplifier, filter and detector for each unipolar electrode, and devices for controlling the stimulation pulses for the heart.

In a cardiac pacemaker of this type, the electrodes can be placed in the atrium and in the ventricle of the heart. The indifferent electrode is formed, for example, by the capsule wall of the pacemaker. Such an electrode system with unipolar electrodes has excellent stimulation and detection characteristics. However, with a system of this type, there is the danger that the smooth functioning of the pacemaker will be impaired by spurious signals caused by muscle spasms or by signals originating outside the body. In order to prevent the signals caused by muscle spasms in the vicinity of the pacemaker capsule from being detected by the pacemaker as cardiac signals, a known method is to insulate nearly the entire capsule and to leave only a small conductive area free of insulation which is faced away from the muscle tissue during implantation. However, this procedure reduces the conductive surface of the indifferent electrode and can result in polarization problems.

SUMMARY OF THE INVENTION

The principal object of the present invention is to devise a simple and secure manner of suppressing all types of spurious signals received by a cardiac pacemaker without having a negative effect on the beneficial stimulation and/or detection characteristics of the pacemaker.

This object is accomplished, according to the invention, by providing the cardiac pacemaker with a signal processing unit which receives the output signals of both detectors and which passes an output signal to the devices for controlling the stimulation impulses unless signals from both detectors are arrive at approximately the same time.

Thus, the present invention is based upon the realization that, in practice, natural cardiac signals are detected by only one electrode at a time. For example, a QRS complex generates an output signal of the detector connected to the electrode that is placed in the ventricle. In contrast, the electrode placed in the atrium records only a negligibly small signal. The relationships are different in the presence of a spurious signal. In such a case, both electrodes record approximately equal signals. The occurrence of equal signals on both electrodes is a definite indication of a malfunction.

In a further refinement of the invention, an additional amplifier with a series-connected detector is connected to receive the signals of both electrodes, after suitable amplification. The output signals of all three detectors are then applied to the signal processing unit. If signals are received simultaneously by the individual electrodes, the signal processing unit prevents the transmission of the output pulse from said processing unit to the devices used to control the stimulation impulses.

The signal processing unit according to the invention can be simply and economically constructed of electronic logic elements. All components for the amplifiers, filters, detectors, and the signal processing unit can be of either analog or digital design.

For a full understanding of the present invention, reference should now be made to the following detailed description of one preferred embodiment of the invention and to the accompanying drawings.

DESCRIPTION OF THE PREFERRED EMBODIMENTS

Figure 2A:
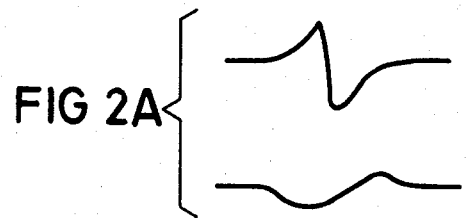
FIGS. 2A, 2B and 2C are signal-versus-time diagrams of signals which may be received by electrodes in the atrium and the ventricle, respectively, of a heart.
Figure 2B:
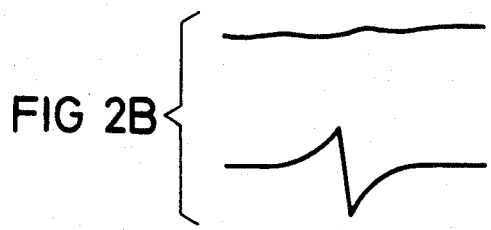
Figure 2C:
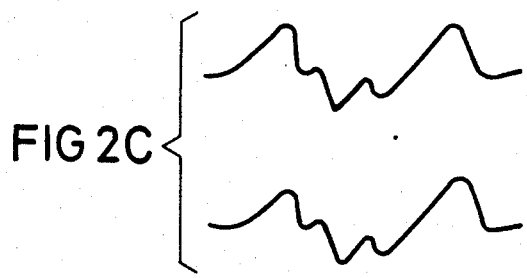

FIGS. 2A, 2B and 2C, respectively, show three pairs of signals where the upper signal in each pair illustrates a signal received from the electrode in the ventricle and the lower signal represents a signal received from the electrode in the atrium of a heart. A QRS complex in the ventricle is assumed as the signal source for the first signal pair (FIG. 2A). The electrode in the ventricle produces the typical signal pattern for this. Due to its relatively large distance from the signal source, the electrode in the atrium produces a practically negligible signal. For the signal pair shown in FIG. 2B, activity in the atrium (P wave) is assumed to be the signal source. In this case, the electrode in the atrium exhibits a strong signal, while the electrode in the ventricle exhibits practically no signal.

For the third signal pair (FIG. 2C) a spurious signal is assumed as the signal source. In this case, both electrodes produce signals of approximately equal strength with signal patterns of corresponding shape.

Figure 1:
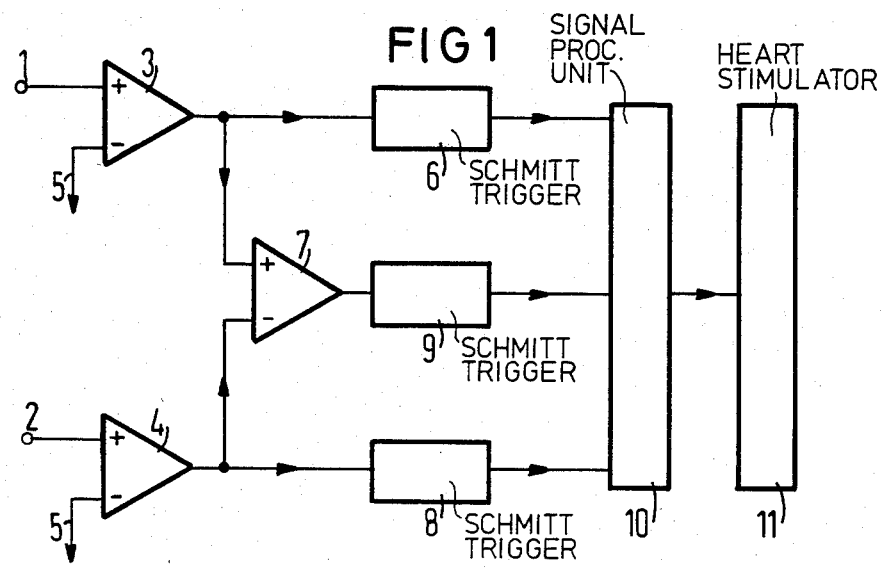
FIG. 1 is a block diagram of a cardiac pacemaker with a spurious signal detector according to a preferred embodiment of the present invention.

FIG. 1 is a block diagram of a cardiac pacemaker according to the invention. Reference numerals 1 and 2 identify the connections for the electrodes in the atrium and ventricle, respectively. Each connection is applied to an input of a separate amplifier 3, 4, respectively. The casing of the cardiac pacemaker, for example, serves as the indifferent electrode 5 for both the atrium electrode and the ventricle electrode. In each case, the indifferent electrode 5 is connected to the other input of the respective amplifiers 3, 4.

Without going into further detail, it is assumed here that the amplifiers may also be equipped with filters.

The output signal of amplifier 3 is applied to a first detector 6 and simultaneously to one input of a differential amplifier 7. The output signal of the amplifier 4 is applied to a second detector 8 and simultaneously to the other input of the differential amplifier 7. The output signal of the differential amplifier 7 is applied to a third detector 9. The three detectors 6, 8 and 9 are threshold gates or "Schmitt triggers" which produce output signals if their respective input signals exceed a prescribed threshold. The three detector output signals are applied to a signal processing unit 10 to which the remaining electronic circuitry of the cardiac pacemaker is connected. This remaining circuitry, which is represented in FIG. 1 by a block 11, does not need to be described in detail. This circuitry can be of a design generally used in the art for bifocal cardiac pacemakers.

As can be seen from the signal patterns shown in FIG. 2, an output signal is supplied by the detector 6 each time that a signal is received by the atrium electrode. Correspondingly, an output signal is supplied by the detector 8 whenever a signal is received by the ventricle electrode. If these signals are caused by actual cardiac activity, a signal at the output of differential amplifier 7 is also produced every time, together with a signal at the output of the additional detector 9. However, in the case of external interference, or of a spurious signal in general, both electrodes produce their signals simultaneously so that the detectors 6 and 8 both supply an output signal, but the detector 9 does not since equal signals are applied to the two inputs of the differential amplifier 7 and, consequently, no output signal is generated.

The manner in which the signal processing unit 10 determines from the output signals of the three detectors 6, 8, and 9 whether actual cardiac activity or interference is involved can best be illustrated using a table:

TABLE

| Type of Signal | Output Signal of Detector |
|---|---|
| P wave | 6 and 9 |
| QRS complex | 8 and 9 |
| Spurious signal | 6 and 8 |

As can be seen from this table, the received signals are indicative of actual cardiac activity when an output signal is supplied by one of the detectors directly assigned to the electrodes and by the additional detector connected to the differential amplifier. However, if an output signal is supplied by both of the detectors assigned to the individual electrodes, interference is indicated. In this case, the signal processing unit 10 prevents a signal for controlling the stimulation impulses from being passed onto the circuitry 11.

Figure 3:
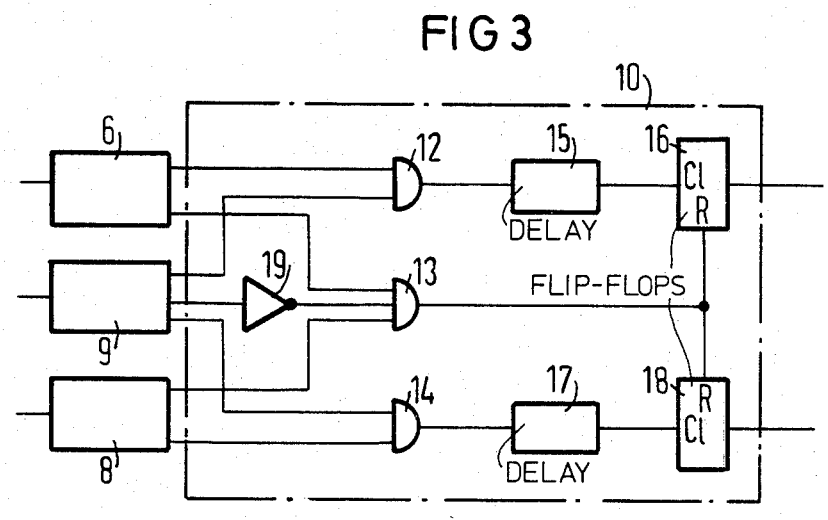
FIG. 3 is a schematic diagram of the signal processing unit employed in the pacemaker of FIG. 1.

A possible design for the signal processing unit 10 is shown as a block diagram in FIG. 3. Detectors 6, 8 and 9 are shown in addition to the processing unit. The signal processing unit contains three logical AND circiits 12, 13 and 14. The output signals of detectors 6 and 9 are applied to logical AND circuit 12; the ouput signals of detectors 6 and 8 and, if desired, that of detector 9 via an inverter 19, are applied to logical AND circuit 13; and the output signals of detectors 8 and 9 are applied to the logical AND circuit 14. The output signal of the logical AND circuit 12 is applied via a delay element 15 to the control input of a flip-flop 16. Correspondingly, the output signal of the logical AND circuit 14 is applied via another delay element 17 to the control input of another flip-flop 18. The output signal of the logical AND circuit 13 is simultaneously applied to the reset inputs of the two flip-flops 16 and 18. In addition, if desired, the output signal of the detector 9 can be applied via an inverter 19 to an additional input of the logical AND circiut 13. This increases the certainty that natural cardiac signals will be treated as such, and not as spurious signals as may sometimes occur.

This signal processing unit 10 operates as follows:

If the signal is based on atrium activity (P wave), the detectors 6 and 9 each supply an output signal. In this case, the logical AND circuit 12 is activated and, after a typically brief delay of a few milliseconds, it switches the output of the flip-flop 16 to high. This signal indicates that a P wave was present. However, if interference occurs, only the logical AND stage 13 will be activated and the two flip-flops 16 and 18 will be reset.

There has thus been shown and described a novel bifocal cardiac pacemaker which fulfills all the objects and advantages sought therefor. Many changes, modifications, variations and other uses and applications of the subject invention will, however, become apparent to those skilled in the art after considering this specification and the accompanying drawings which disclose preferred embodiments thereof. All such changes, modifications, variations and other uses and applications which do not depart from the spirit and scope of the invention are deemed to be covered by the invention which is limited only by the claims which follow.

What is claimed is:

1. In a cardiac pacemaker comprising (a) two unipolar electrodes; (b) one indifferent electrode, (c) a series-connected amplifier and detector coupled to each of said unipolar electrodes, and (d) means for generating and controlling heart stimulation pulses in dependence upon the ouput signals of said detectors; the improvement comprising signal processing means, responsive to said output signals of said detectors, for suppressing the application of said output signals to said means for generating heart stimulation pulses when both of said detectors produce output signals at substantially the same time.

2. The pacemaker defined in claim 1, further comprising a series-connected additional amplifier, having inverted and non-inverted inputs, and an additional detector, the inverted input of said additional amplifier being connected with the output of one of said detectors, the non-inverted input of said additional amplifier being connected with the output of the other of said detectors, said signal processing means being responsive to said output signals of said two detectors as well as said additional detector to permit the application of said output signals of said two detectors to said means for generating heart stimulation pulses if and only if output signals are produced by one of said two detectors as well as said additional detector.

3. The pacemaker defined in claim 2, wherein said signal processing means comprises logical elements.

4. The pacemaker defined in claim 1, wherein said signal processing means comprises logical elements.

5. The pacemaker defined in claim 4, wherein said logical elements and at least parts of the amplifiers, detectors and filters are digital circuits.

* * * * *